US00PP14548P39

(12) United States Plant Patent
Chiamori

(10) Patent No.: US PP14,548 P3
(45) Date of Patent: Feb. 17, 2004

(54) NECTARINE TREE NAMED 'WHITE DRAGON'

(50) Latin Name: *Prunus persica*
Varietal Denomination: White Dragon

(76) Inventor: Patrick Chiamori, 9588 S. Lac Jac Rd., Reedley, CA (US) 93654

( * ) Notice: Subject to any disclaimer, the term of this patent is extended or adjusted under 35 U.S.C. 154(b) by 0 days.

(21) Appl. No.: 10/027,127

(22) Filed: Dec. 19, 2001

(65) Prior Publication Data

US 2003/0115648 P1 Jun. 19, 2003

(51) Int. Cl.[7] ..... A01H 5/00
(52) U.S. Cl. ..... Plt./188

(58) Field of Search ..... Plt./188

(56) References Cited

U.S. PATENT DOCUMENTS

PP8,534 P 1/1994 Chiamori et al. ..... Plt./41.4

*Primary Examiner*—Anne Marie Grunberg
(74) *Attorney, Agent, or Firm*—Mark D. Miller

(57) ABSTRACT

A new and distinct nectarine which is somewhat similar to the 'Sunny Red' nectarine tree (U.S. Plant Pat. No. 8,534) from which it is a sport but from which it is distinguished by producing a later ripening fruit which are mature for harvesting and shipment approximately 3 to 5 days after the 'Sunny Red' nectarine, as well as being white fleshed as compared to the yellow fleshed fruit of 'Sunny Red.'

1 Drawing Sheet

(*Prunus persica* var. Nectarine).

BACKGROUND OF THE INVENTION

The present invention refers to and relates to a new and distinct variety of nectarine tree which will hereinafter be denominated varietally as the 'White Dragon' nectarine tree which produces a clingstone fruit, which are mature for commercial harvesting and shipment approximately September 7–10 in the San Joaquin Valley of Central California as a late, fresh-market nectarine, white fleshed with a good red blush skin coloration.

In the development of new varieties of fruit trees a premium is placed upon those which produce fruit either early or late in the growing season when few competing varieties are available. When a new variety of fruit which matures early or late has good size, good color (blush), good flavor, and can be held or stored well, the fruit of this variety has a very good chance for commercial success in the fresh market. This new invention of a white fleshed nectarine meets this criteria.

Origin and Sexual Reproduction of the New Variety

The present variety of nectarine tree was discovered by the inventor in his orchard of 'Sunny Red' nectarine trees (U.S. Plant Pat. No. 8,534) which is located near Reedley, Calif. in the San Joaquin Valley of Central California. The inventor discovered the variety as a sport of a 'Sunny Red' nectarine tree in 1998. The new variety was first reproduced by the inventor in 1999 at 9588 Lac Jac Road in Reedley, Calif. by hybrid grafting 12 trees from mature wood. The asexually reproduced trees first bore fruit of the new variety in September 2000. The inventor carefully compared the asexually reproduced trees with the parent sport including the fruit thereof and has confirmed that the parent and the progeny are identical in all respects.

BRIEF SUMMARY OF THE INVENTION

The 'White Dragon' nectarine tree is characterized by producing a clingstone fruit which has good red blush coloration and is ripe for commercial harvesting and shipment approximately September 7–10 in the San Joaquin Valley of Central California. The new variety is most closely similar to the 'Sunny Red' nectarine tree (U.S. Plant Pat. No. 8,534) from which it is a sport but from which it is distinguishable in that it ripens about 3 to 5 days later than the fruit of the 'Sunny Red' nectarine tree and in that the fruit is 10% to 15% larger in size than that of the 'Sunny Red' nectarine tree.

BRIEF DESCRIPTION OF THE DRAWING

The accompanying drawing is a color photograph showing several fruit of the new variety including the first in bottom view showing the apex end, the second in top view showing the stem cavity, the third in side view showing the surface, the fourth in side view to display the blush color, and the fifth to show a section fruit displaying the flesh and the pit cavity. The stone (or pit) is also displayed along with typical foliage of the new variety.

DETAILED BOTANICAL DESCRIPTION

Referring more specifically to the pomological details of this new and distinct variety of nectarine tree the following observations have been made for the ecological condition prevailing at the orchard of origin which is located near Reedley, Calif. in the San Joaquin Valley of Central California. All major color designations are by reference to the Dictionary of Color by Maerz and Paul, First Edition, 1930. Common color names are also occasionally employed.

Tree

Generally develops and grows similar or equivalent to that of the parent 'Sunny Red' nectarine tree.

Vigor: Good.
Figure: The tree is upright to upright spread.
Productivity: Productive.
Regularity of bearing: Regular under the ecological conditions of the Central San Joaquin Valley.

Trunk

Size: Small to medium and the circumference taken approximately 10" above ground is 7.08 inches. Tree is 3 years old.
Surface texture: Moderately rough.
Color code: Log cabin (15-A-5).
Lenticels:
*Number.*—Approximately 10 per inch on the branches.
*Size.*—9–10 mm (0.35–0.39 inch) on average.

Branches

Size: Small to medium; circumference of branches, approximately 20" above ground is 3.93 inches.
*Scaffolds.*—3 to 4.
*Angle of branches.*—38°.
Surface texture:
*a.. Mature.*—Relatively smooth.
*b. Immature.*—Smooth.
Color code: One year or older — Castilian Brown (7-J-9).
*Immature.*—Vividine Green (17-I-6).

Leaves

Size: Medium to large.
Length: 122–136 mm. (4.80–5.35 inch).
Width: 40–44 mm. (1.57–1.73 inch).
Shape: Lanceolate — leaf tip acuminate.
Color code: a. Upwardly disposed surface, Chrome Green (23-H-12). b. Downwardly disposed surface, Parent Ar. (21-I-6).
Marginal form: Generally crenate.
Leaf vein:
*a. Color code.*—Callistre Green (19-L-6).
*b. Thickness.*—2 mm (0.08 inch).
Glandular characteristics: Reniform.
Petiole:
*Length.*—10–14 mm. (0.39–0.55 inch).
*Thickness.*—2–2½ mm. (0.08–0.1 inch).
Stem glands:
*Stipules.—Small to medium, oblong to ovate —reddish brown, M&S Green (*7-B-1).

Flowers

Flower buds:
*Length.*—Medium — Average 10 mm (0.39 inch).
*Form.*—Plump, somewhat conic shape.
*Pubescence.*—Pubescent.
*Bud scales.*—Very pubescent.
Flowers: Showy.
*Size.*—Medium diameter, average 34 mm (1.34 inch).
Pollen: Present, self fertile.
Petals: Number — 5.
*Length.*—Average 14 mm (0.55 inch).
*Width.*—Average 14 mm (0.55 inch).
*Margins.*—Slightly wavy.
Sepals: 5 broadly acute — Peony, Burmese Ruby (7-H-6).
Fragrance: Very slight.
Blooming period: March 10 to March 17.
Bloom color: Light pink (1-B-3).
Anthers: Number — ranges from 25 to 30.
Stamens: Length 10–12 mm (0.39–0.47 inch).
Filament: Light pink (1-H-4).
Pistil: Average 18 mm (0.71 inch).
*Color.*—Near Water Green (19-B-2).

Fruit

Date of maturity: September 7–10.
Size:
*Diameter axial plane.*—66.68–82.55 mm. (2.85–3.25 inch).
*Transverse in suture plane.*—66.68–75.61 mm. (2.63–2.94 inch).
*Transverse at right angles to suture plane.*—61.9–69.85 mm (2.44–2.75 inch).
Form:
*Uniformity.*—Uniform.
*Symmetrical/asymmetric.*—Symmetrical.
*Suture.*—small with reddish orange, Meadow Pink (5-A-5).
*Ventricle surface.*—Slightly uneven.
*Stem cavity.*—Width — 25 mm. (0.98 inch). Depth — 9–10 mm. (0.35 inch). Length — 35 mm. (1.37 inch). Shape — ovate.
*Stem short.*—Caliper — 4 mm. (0.16 inch).
*Apex.*—Slightly rounded.
*Pistil point.*—Retuse.
Skin:
*Thickness.*—Thin.
*Texture.*—Firm.
*Tendency to crack.*—Not evident.
*Color code.*—a. Blush color — reddish (46-H-5). b. Ground color — Brass (11-L-6).
*Flesh color.*—Popcorn (9-J-3) — there is a yellow area running from the epidermis along the suture line to the pit well, in the suture line itself (not illustrated in drawing because of cut along suture line) — Empire (9-K-3). Near the pit — reddish (42-L-1).
*Color of pit cavity.*—Same color as flesh near pit.
*Color of pit well.*—Near Dahlid (43-L-6).
*Juice production.*—Very good.
*Flavor.*—Very good.
*Aroma.*—Moderate.
*Texture.*—Firm.
*Fibers.*—See under stone.

Stone

Free or cling: Clingstone.
Fibers:
*Numbers.*—Many.
*Length.*—6–13 mm. (0.23–0.51 inch).
Size:
*Length.*—35–37 mm (1.37–1.46 inch).
*Width.*—25–32 mm. (0.98–1.26 inch).
*Thickness.*—20–30 mm. (0.79–1.18 inch).
Form: Ovate.
Apex shape: With slightly pointed tip.
Color code (dry): Wineberry (55-H-4).
Base: Nearly flat.
Sides: Slightly uneven, ventral edge relatively narrow, fourth groove produces a low reed on basal end.
Ridges: Grooves — particularly on apical end.

Tendency to split: Not known.
Use: Fresh market commercially.
Keeping quality: Very good.
Resistance to disease: Unknown.
Harvesting: September 7–10.

Although the new variety of nectarine tree possesses the characteristics described above under the growing conditions prevailing near Reedley, Calif. in the Central San Joaquin Valley of California, it is to be understood that variations of the usual magnitude and characteristics as a result of change in growing conditions, irrigation, fertilization, pruning, pest control, climatic variation etc. are expected.

Having thus described and illustrated my new variety of nectarine tree, what I claim as new and desire to be secured by Plant Letters Patent is:

1. A new and distinct variety of nectarine tree substantially as illustrated and described which is somewhat nearly similar to the 'Sunny Red' (U.S. Plant Pat. No. 8,534) from which it is a sport but from which it is distinguished by producing a later maturing fruit with good coloration, white fleshed with good edible quality, which matures for commercial harvesting and shipment September 7–10 or about 3–5 days after the fruit of 'Sunny Red.'

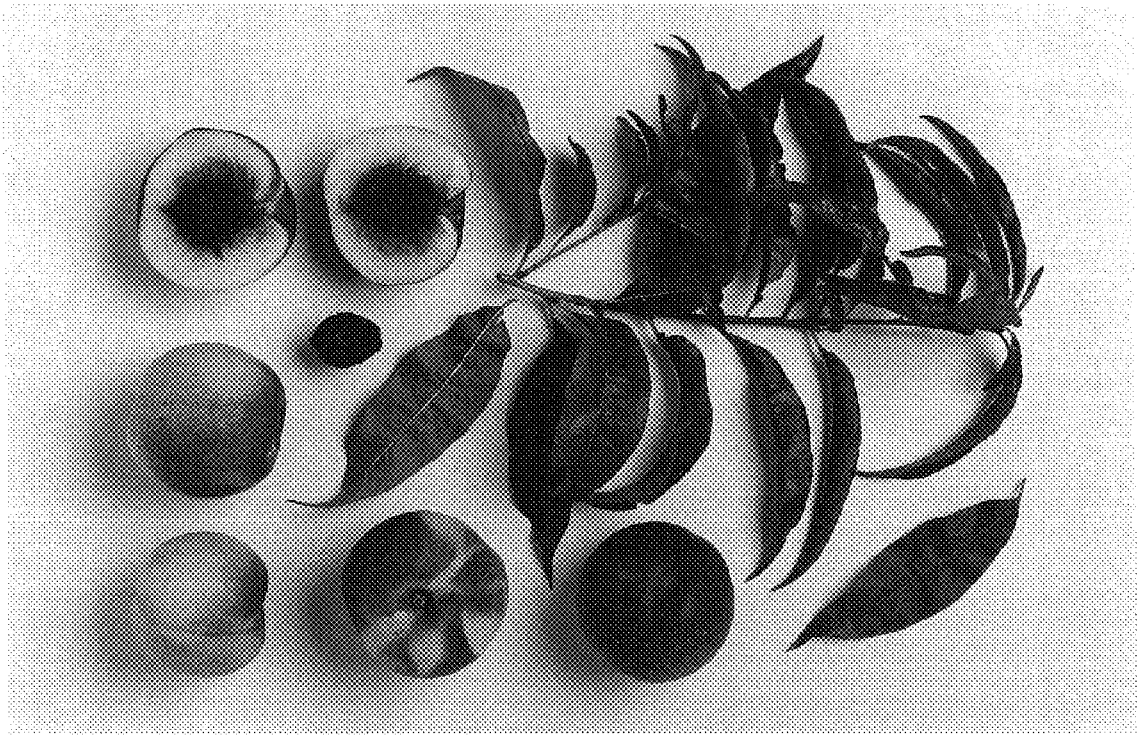

* * * * *